(12) United States Patent
Hurd

(10) Patent No.: US 8,478,432 B2
(45) Date of Patent: Jul. 2, 2013

(54) AGENTS AND METHODS FOR RELIEVING MUSCLE SPASMS

(76) Inventor: Stanley M. Hurd, Hamden, CT (US)

(*) Notice: Subject to any disclaimer, the term of this patent is extended or adjusted under 35 U.S.C. 154(b) by 830 days.

(21) Appl. No.: 11/653,669

(22) Filed: Jan. 16, 2007

(65) Prior Publication Data

US 2007/0168002 A1    Jul. 19, 2007

Related U.S. Application Data

(60) Provisional application No. 60/760,127, filed on Jan. 18, 2006.

(51) Int. Cl.
*A61N 1/44* (2006.01)

(52) U.S. Cl.
USPC .......................................... 607/152; 607/115

(58) Field of Classification Search
USPC ............................ 607/2, 115, 152
See application file for complete search history.

(56) References Cited

U.S. PATENT DOCUMENTS

| | | | | |
|---|---|---|---|---|
| 4,848,348 A * | 7/1989 | Craighead | | 600/396 |
| 5,050,595 A * | 9/1991 | Krafft | | 607/108 |
| 5,405,366 A * | 4/1995 | Fox et al. | | 607/50 |
| 5,458,627 A * | 10/1995 | Baranowski et al. | | 607/51 |
| 5,779,632 A * | 7/1998 | Dietz et al. | | 600/391 |
| 5,944,740 A * | 8/1999 | Inoue et al. | | 607/1 |
| 6,694,185 B2 * | 2/2004 | Orton | | 607/2 |
| 2002/0193832 A1 * | 12/2002 | Gray | | 607/3 |
| 2005/0085706 A1 * | 4/2005 | Perrault et al. | | 600/391 |
| 2007/0208130 A1 * | 9/2007 | Sasahara et al. | | 524/521 |

* cited by examiner

*Primary Examiner* — Joseph Dietrich
(74) *Attorney, Agent, or Firm* — Bachman & LaPointe, P.C.

(57) ABSTRACT

A method of affecting metabolic function is presented which utilizes a conductive coating, film, or covering on a body tissue to distribute electrical charge, either passively or in conjunction with applied electrical energy.

10 Claims, 1 Drawing Sheet

AGENTS AND METHODS FOR RELIEVING MUSCLE SPASMS

CROSS-REFERENCE TO RELATED APPLICATION(S)

The present application claims the benefit of U.S. Provisional Patent Application 60/760,127, filed on Jan. 18, 2006, to a FORMULATION FOR RELIEVING MUSCLE SPASMS

BACKGROUND OF THE INVENTION (1) Field of the Invention

The present invention relates to agents and to methods for affecting metabolic function and in particular to a conductive coating, film, or covering on a body tissue to distribute electrical charge, either passively or in conjunction with applied electrical energy.

(2) Prior Art

The electrophysiological nature of neural transmission is well known. However, certain evidence suggests that there are electrophysiological mechanisms functioning at the level of entire organs or tissues. For example, acupuncture, which appears to have at least an electrophysiological component, has been recognized by the National Institutes of Health as effective in treating a variety of disorders (NIH Consensus Statement, Acupuncture, National Institutes of Health, 15, 1-34, 1997) and must work on a scale much larger than that which has been rigorously studied at the cellular level. In this field, metal needles are introduced through the skin into the deeper tissues, and manipulated either manually or electrically or both. By this means, various effects on physiology are produced. For example, acupuncture has been shown to produce anesthesia, reduce nausea, ameliorate dysmenorrhea, and lessen the symptoms of asthma, most of which effects are produced at considerable distance from the point of needle insertion. That this is purely an electrophysiological effect is not clear, as the acupuncture literature imputes the effects to a bodily energy known as chi; additionally, certain procedures have been shown to produce effects within the central nervous system (see, e.g., *Neurobiology of Acupuncture*, Ma, S., eCAM, 1:1 41-47, 2004). However, as was concluded in the NIH Consensus Statement, it is clear that needling does affect body functions and that the body's tissues have varying levels of conductivity and electrical charge.

In manipulating the needles, the acupuncturist is said to transfer his or her own chi to the patient, and it is thought by some that this transfer is actually a flow of electrical energy (*Electrophysiology and the Acupuncture Systems*, Starwynn, D., Medical Acupuncture, 13:1, 2006). In addition to manually manipulated needles, electrical stimulation of acupuncture points has been used extensively. Some of the means of stimulation have used electrodes rather than needles (see, for example, U.S. Pat. No. 6,691,622). This patent relates to the use of electrically conductive means. This patent suggests that increasing the ability of charge to disperse at the various acupuncture points on the body may increase the efficacy of acupuncture techniques.

It has been demonstrated that the body generates endogenous electric fields in response to wounding (see, for example, *Electrical signals control wound healing through phosphatidylinositol-3-OH kinase-γ and PTEN*, Zhao, M. et al, Nature 442, 457-460, 2006). That such fields exist in the body, and that manipulation of them by externally applied electrical energy can affect the rate of healing, argues strongly that electrophysiological effects at a macroscopic level play an important role in regulating metabolic function.

Another bit of evidence from folk medicine is the reported use of a bar of soap to relieve nocturnal leg-muscle cramps. Since it is reportedly not necessary for the soap to touch the skin in order to be effective, it is hard to see by what possible mechanism such an effect might be mediated until it is recognized that ionic surfactants, a major component of most commercial soaps, are very effective at dispersing static electrical charge. The dispersion of surface charge has not been shown previously to have any effect on cramping or any other metabolic condition, but in the absence of any other plausible physical mechanism for this effect it does suggest a possible electrophysiological mechanism operating at a larger scale than has been widely appreciated until recently.

Techniques exist that include conductive means attached to the skin, such as electrodes, to monitor electrochemical events within the body (see, for example, U.S. Pat. No. 6,434, 410). Electrolytic gels and solutions provide a conductive interface between the skin and external devices. These devices are constructed to interact minimally with the electric fields of the body, being rather means for measuring or monitoring such electric fields.

Other known techniques relate to the use of conductive means in alleviating muscular pain and other conditions. U.S. Pat. No. 5,944,740, for example, relates to the use of what is essentially a flat battery attached to the surface of the skin to cause electric current to flow through the skin and into the deeper tissues. This is a small, discrete device that generates an active voltage differential to achieve its effect. It is specifically configured to deliver electrical energy from an external source via discrete and limited electrode shapes using electrodes of alternating polarity in close proximity to each other. It is also relatively large in cross section, making it conspicuous in everyday use.

U.S. Pat. No. 4,398,545 relates to the use of a self-adhesive bandage with a flexible, electrically conductive inner surface coupled to an electrical stimulation unit to block pain via TENS. This technology is well known in the open medical literature, but briefly involves pulses of electrical energy applied to the patient's skin in order to create low current pulses and magnetic fields within the patient's body which block neural pain transmission. This and other such devices, including electrodes used specifically in electrically stimulating acupuncture points, see U.S. Pat. No. 6,691,622, are configured to deliver electrical energy from external sources via discrete and limited electrode shapes using electrodes of alternating polarity in close proximity to each other. They, too, have a substantial cross-sectional area and are obtrusive in everyday use.

U.S. Pat. No. 5,785,040 relates to the use of a highly-conductive gel on the surface of the skin, coupled to an electrode, to provide a means of either applying electrical energy to the body or to monitor electrical fields within the body. It uses a clear, disposable gel means that is easily positioned and removed from the body in conjunction with a washable, permanent electrode means for connection to the appropriate medical devices. This is intended for use with such systems as those contemplated or supported in U.S. Pat. Nos. 4,398,545, 6,434,410, and 6,691,622. Also, the applied gel must be made thick enough for easy manipulation, and so would be conspicuous and awkward to secure in place in everyday use.

U.S. Pat. No. 3,911,910 relates to the use of electrodes attached to the body to relieve spasticity in limbs by sensing spastic contractions and applying current pulses to cause the antagonistic muscles to contract. This does not directly relieve cramping or spasm, but rather overcomes the contraction by stimulating the opposing muscles to stretch out the affected muscle. In addition, its electrode means are discrete, limited in size, and must be carefully positioned to properly contract the only those muscles opposing the cramped muscle.

SUMMARY OF THE INVENTION

It is therefore an aim of the current invention to provide a means of distributing, dispersing, and/or manipulating electrical charge over or within areas of the body, said areas tending to be on the scale of whole muscles or organs.

It is another aim of the current invention to establish a method of altering metabolic function by such means of distributing, dispersing and/or manipulating electrical charge.

It is yet another aim of the current invention to provide such means that would passively distribute charge according to innate voltage differentials within the body.

It is yet another aim of the current invention to provide such means that would augment the distribution of charge in the body by using external electrical means.

It is yet another aim of the current invention to provide such means that would be long lasting.

It is yet another aim of the current invention to provide such means that would be flexible.

It is yet another aim of the current invention to provide such means that would conform closely to the surface to which it is applied.

It is yet another aim of the current invention to provide such means that can be readily shaped to conform to the needs of the instant application.

It is another aim of the current invention to provide such means that would be thin enough in cross section to be unobtrusive in everyday use.

In the current invention, it has been found that by providing conductive means to allow charge to distribute passively over extended areas of the surface of the skin a considerable degree of relief can be obtained from muscle cramps, spasms and the associated pain, as well as relief from pain having no apparent association with muscle activity, such as migraine and sinus headaches. Optimally such means should be long lasting, flexible and, for maximum comfort, be as unobtrusive as possible. By extension, the use of such means within the body would require very similar characteristics. Further, such means may be capable of being shaped such that its borders may be altered to match the needs of each instant application.

In a first aspect, the present invention relates to an agent for distributing, dispersing and/or manipulating electrical charge over or within areas of a body. The agent broadly comprises a conductive coating formulation for use on a skin surface.

In a second aspect, the present invention relates to an agent for distributing, dispersing and/or manipulating electrical charge over or within areas of a body. The agent broadly comprises a conductive fabric having a conductive material applied to a non-conductive fabric.

In a third aspect, the present invention relates to an agent distributing, dispersing and/or manipulating electrical charge over or within areas of a body. The agent broadly comprises a non-reactive metallic film applied directly to tissues.

In a fourth aspect, the present invention relates to a method for treating muscle spasms and/or affecting metabolic function broadly comprising the steps of creating a conductive coating formulation, and applying the conductive coating formulation to a skin surface.

In a fifth aspect, the present invention relates to a method for treating muscle spasms and/or affecting metabolic function broadly comprising the steps of providing a conductive fabric and placing the conductive fabric over an area afflicted with a cramp. The conductive fabric may be constructed by applying a conductive coating to a non-conductive fabric, or by using conductive fibers in weaving the fabric.

In a sixth aspect, the present invention relates to a method for affecting metabolic function broadly comprising the steps of providing a non-reactive metallic film and applying the metallic film directly to tissue.

Other details of the agents and methods for relieving muscle spasms and/or affecting metabolic function of the present invention, as well as other objects and advantages attendant thereto, are set forth in the following detailed description.

DETAILED DESCRIPTION OF THE PREFERRED EMBODIMENT(S)

Figure 1:
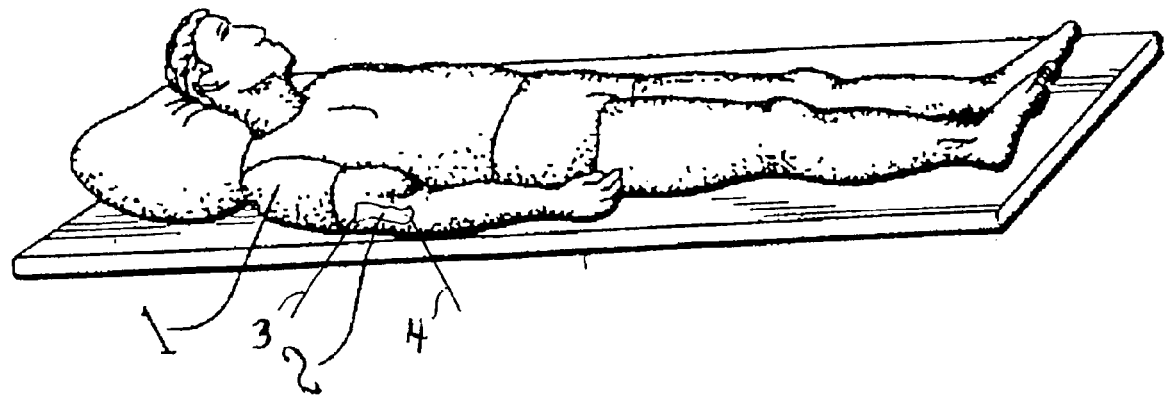
FIG. 1 is a schematic representation of a person having a conductive coating formulation applied to his skin.

In accordance with the present invention, there is provided a means for relieving muscle spasms and/or altering metabolic function. The means in a first embodiment shown in FIG. 1 broadly comprises a conductive coating formulation for use on the surface of the skin of a person 1. The conductive coating 2 may comprise an aqueous solution of protein isolate, one or more surfactants, one or more simple salts, one or more humectants to maintain moisture content, one or more non-hydrophobic emollients to improve skin feel, and one or more preservatives to prolong shelf life. Functionally, the protein isolate provides the conductive substrate of the coating 2, the simple salt(s) provide charge carriers, and the surfactant(s) provide intimate contact with the skin. Other poly-ionic molecules of high molecular weight may be substituted for the protein isolate(s); however, the poly-ionic molecules should be non-toxic and hypoallergenic. Various simple salts including, but not limited to, NaCl, $CaCl_2$, and KCl, may be used as charge carriers. The use of ionic surfactants is of benefit in that they will provide additional conductivity to the coating 2. Humectants serve to maintain sufficient water content to allow charge to move freely. The conductive coating formulations described herein may be used to disperse charge between contiguous areas of the skin, or may be used to connect more distant areas when used in conjunction with wires or other conductive means 3, 4.

In one embodiment of a conductive coating formulation, the concentration of the conductive substrate may be within the range of from 5.0 to 25% wt/vol., the total concentration of the simple salt(s) can be within the range of 10 to 30% wt/vol, the concentration of the humectant(s), depending on the exact nature of the humectant chosen, can be in the range of from 1.0 to 10% wt/vol in total, and the concentration of surfactant(s) can be within the range of from 5.0 to 30% wt/vol in total depending on the nature of the particular surfactant(s) chosen.

Other ranges for the other constituents of the conductive coating formulation may be appropriate when alternative components have been identified and used. The exact chemical nature and relative concentrations of emollients and preservatives has no significant impact on the efficacy of the formulation.

One particular embodiment of a conductive coating formulation which has been found to be useful comprises an aqueous solution containing 15% wt/vol whey protein isolate, 10% wt/vol NaCl, 3.0% wt/vol glycerin, 7.5% wt/vol cocamidopropyl betaine, 2.1% wt/vol sodium lauryl ether sulfate, 2.1% wt/vol sodium lauryl sulfate, 10% wt/vol aveno sativa isolate, 0.55 wt/vol carbomer 940, 0.1% wt/vol lyophyllized aloe vera, 0.5% wt/vol sodium citrate, 0.1% wt/vol EDTA, and 0.1% wt/vol methylparaben. This embodiment has its greatest conductivity at about 70% relative humidity, which humidity is consistent with that at the surface of the skin.

When used to alleviate muscle cramps, the above embodiment of the conductive coating formulation may be applied as a lotion to the surface of the skin and spread over the length of the affected muscle. This embodiment usually relaxes cramped muscles within 1.0 to 2.0 minutes.

The use of either the ionic surfactants or a combination of protein and simple salts are each effective in reducing cramping, with the conductivity of the final film being the controlling factor for efficacy. Relative conductivity of the conductive coating films in accordance with the present invention was determined by a device consisting of two inert, parallel wire electrodes 2 cm long attached to a flat, insulating surface and separated by a 2 cm space. The aqueous solutions of varying composition and ionic strength were applied between the electrodes and allowed to dry. Resistance was measured as the analog of conductivity, the nature of the conductive coating films making them refractory to standard measures of conductivity. Efficacy was measured separately for each solution and was determined by self-reporting by the subjects on a 1-5 scale.

As the conductive coating films dried, the resistance decreased substantially, probably owing to the increase of ionic strength as the water was removed. The films initially showed a resistance of over 1.0 meg ohm and reached a minimum resistance of 40-50 k ohm at approximately 70% relative humidity. It was found that conductive coating films having resistance minima at around 500 k ohm or greater lost their efficacy in relieving cramping. Therefore, it appears to be best if the composition of the conductive coatings be adjusted such that their resistance in this test apparatus be in the range of 0-200 k ohm at 70% relative humidity. These results show that not only is conductivity the primary means of establishing efficacy but that the exact chemical nature of the film is of secondary importance.

Figure 2:
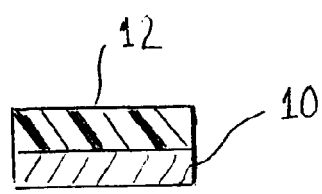
FIG. 2 is a schematic representation of a first embodiment of a conductive fabric.
Figure 3:
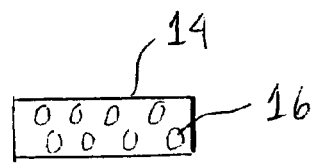
FIG. 3 is a schematic representation of a second embodiment of a conductive fabric.

Another embodiment of the present invention, as shown in FIGS. 2 and 3, consists of conductive fabrics made either by applying a conductive inner surface 10 to a non-conductive fabric 12, or by making the fabric 14 itself out of conductive materials 16 such as graphite fiber or metallic threads. Such fabrics can be made into clothing to be worn over areas commonly afflicted with muscle cramps such as the back and shoulders, or, in the case of nocturnal leg cramps, such fabrics could be made into either pajamas or bed linens. If desired, an electric current could be applied to the conductive fabric using any suitable means known in the art.

Figure 4:
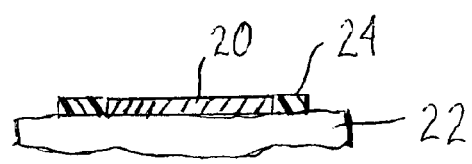
FIG. 4 is a schematic representation of a conductive coating film.

Another embodiment of the present invention as shown in FIG. 4 is to apply non-reactive metallic films 20, such as gold or stainless steel, directly to the tissues 22. This would be particularly useful when working with deep tissues, where a benign, non-reactive, and permanent or semi-permanent film is needed. When such application is performed in deep tissues the films 20 would be surgically inserted and arranged so as to be in contact with the appropriate tissues. In some cases it may be necessary to use a conductive coating film 20 with portions of one or both sides coated with insulating materials 24 to direct current flow more precisely. Such films 20 may be shaped to conform to individual tissues 22, or to follow conductive paths within the body, or even to connect two or more tissues distant from each other within the body. Appropriate insulating materials 24 would be polytetrafluoroethylene (PTFE, Teflon), and polypropylene, among others.

Another aspect of the present invention combines the use of an acupuncture needle (not shown) connected to a conductive coating film 2. By providing a more extensive sink for electrical current than either the acupuncturist's fingers or the small surface connection between the needle and the patient's skin, the flow of electric current would be augmented. The conductive coating film 2 may be either local, with the needle projecting through it into the skin, or it may be distant, either on the patient's body or on that of the acupuncturist, with the needle connected to it by wires or other conductive means (not shown).

The conductive coating film formulations of the present invention may be topically applied to the afflicted area or to tissue overlying or adjacent to the area to be affected. The formulations are designed to establish a conductive coating when applied to the skin, to minimize any irritation caused by direct, prolonged exposure to ionic surfactants, and to minimize any discomfort associated with the application.

In accordance with the present invention, there has been provided agents and methods for relieving muscle spasms and/or affecting metabolic function which fully satisfy the objects, means, and advantages set forth hereinbefore. While the present invention has been described in accordance with specific embodiments thereof, other unforeseeable alternatives, modifications, and variations may become apparent to those skilled in the art having read the foregoing description. Accordingly, it is intended to embrace those unforeseeable alternatives, modifications, and variations as fall within the broad scope of the appended claims.

What is claimed is:

1. A method for distributing, dispersing, and/or manipulating an internal, innate electrical charge within intrinsic areas of a body, comprising the steps of:
   providing an agent comprising a conductive coating formulation;
   wherein said conductive coating formulation comprises an aqueous solution of a means for providing a conductive substrate, at least one surfactant, at least one simple salt for providing a charge carrier, and at least one humectant for maintaining moisture content, and wherein said means for providing a conductive substrate is present in an amount from 5.0 to 25% wt/vol, said at least one simple salt is present in an amount from 10 to 20% wt/vol, said at least one humectant is present in an amount from 1.0 to 10% wt/vol and said at least one surfactant is present in an amount from 5.0 to 30% wt/vol; and
   applying said agent as a lotion on a skin surface, whereby said conductive coating formulation passively manipulates internal electrical fields within the body.

2. The method according to claim 1, wherein said coating further comprises at least one non-hydrophobic emollient to improve skin feel.

3. The method according to claim 1, wherein said coating further comprises at least one preservative to prolong shelf life.

4. The method according to claim 1, wherein said conductive substrate providing means comprises a protein isolate.

5. The method according to claim 1, wherein said conductive substrate providing means comprises poly-ionic molecules.

6. The method according to claim 1, wherein said at least one simple salt is selected from the group consisting of NaCl, CaCl2, and KCl.

7. The method according to claim 1, wherein said conductive coating formulation comprises an aqueous solution containing 15% wt/vol whey protein isolate, 10% wt/vol NaCl, 3.0% wt/vol glycerin, 7.5% wt/vol cocamidopropyl betaine, 2.1% wt/vol sodium lauryl ether sulfate, 2.1% wt/vol sodium lauryl sulfate, 10% wt/vol aveno sativa isolate, 0.55% wt/vol carbomer 940, 0.1% wt/vol lyophyllized aloe vera, 0.5% wt/vol sodium citrate, 0.1% wt/vol EDTA, and 0.1% wt/vol methylparaben.

8. The method according to claim 1, wherein said conductive coating formulation has an electrical resistance in the range of from 0 to 200 k ohm at 70% relative humidity.

9. The method according to claim 1, wherein said agent passively distributes charge according to innate voltage differentials within the body.

10. The method according to claim 1, wherein said conductive coating formulation disperses charge between contiguous areas of the skin.

\* \* \* \* \*